United States Patent [19]

Higuchi

[11] 4,252,790

[45] Feb. 24, 1981

[54] METHOD FOR TREATING GASTRIC ULCER-PRONE PATIENTS

[75] Inventor: Takeru Higuchi, Lawrence, Kans.

[73] Assignee: INTERx Research Corporation, Lawrence, Kans.

[21] Appl. No.: 517,151

[22] Filed: Oct. 23, 1974

Related U.S. Application Data

[63] Continuation of Ser. No. 357,640, May 7, 1973, abandoned.

[51] Int. Cl.³ .............................................. A61K 31/74
[52] U.S. Cl. ...................................................... 424/79
[58] Field of Search .......................................... 424/79

[56] References Cited

U.S. PATENT DOCUMENTS

| 3,007,847 | 11/1961 | Phillips et al. | 424/79 |
| 3,499,960 | 3/1970 | Macek et al. | 424/79 |
| 3,624,209 | 11/1971 | Granatek et al. | 424/79 |

FOREIGN PATENT DOCUMENTS

| 221368 | 1/1958 | Australia | 424/81 |
| 914630 | 1/1963 | United Kingdom | 424/79 |
| 1181003 | 2/1970 | United Kingdom | 42A/79 |

OTHER PUBLICATIONS

Fisher et al.-(The New England Journal of Medicine, 288, No. 6, pp. 273-276, 2/8/73.
Scudamore et al.-Amer. Journal Gastroenterology, vol. 60, No. 1, pp. 9-22, Jul. 1973.
Black et al., Journal of Gastroenterology, vol. 61, No. 6, Dec. 1971, pp. 821-825.

*Primary Examiner*—Frederick E. Waddell
*Attorney, Agent, or Firm*—Burns, Doane, Swecker & Mathis

[57] ABSTRACT

Gastric ulcer-prone patients are treated by introducing into the stomach thereof an effective amount of a non-toxic, non-absorbable active agent, preferably an anion exchange resin having strong hydrophobic binding tendencies (e.g., a styrene-divinylbenzene copolymer bearing quaternary ammonium functional groups), or a hydrophobic, nonionic polymeric adsorbent, capable of effectively binding free and conjugated bile acids present in the stomach as a result of duodenogastric regurgitation.

14 Claims, No Drawings

METHOD FOR TREATING GASTRIC ULCER-PRONE PATIENTS

This is a continuation of application Ser. No. 357,640, filed May 7, 1973, now abandoned.

BACKGROUND OF THE INVENTION

The present invention relates to a method for treating patients which are prone to contracting gastric ulcers, and more especially to a method for compensating for the propensity of such patients to have deleterious amounts of bile acids present in the stomach as a result of duodenogastric regurgitation.

Because it is thought that gastric ulcer, and by gastric ulcer is meant an ulcer located in the stomach as opposed to other portions of the gastrointestinal tract, is caused primarily by the action of ulcerogenic factors such as hydrochloric acid and pepsin which disturb the mucous membrane forming the inner lining of the stomach, conventional pharmaco-therapeutical efforts aimed at the treatment of gastric ulcers have heretofore concentrated on controlling the action of hydrochloric acid and pepsin. Specifically, hitherto-known methods for treating gastric ulcer have been directed toward the inhibition of gastrointestinal motility and secretion, the blocking of spasm and the neutralization or counteraction of hydrochloric acid in the gastric juice. There exists also one school of thought contending that gastric ulcer is caused by abnormal action of the central nervous system, and accordingly, treatment by means of various sedatives and/or tranquilizers has been proposed; however, there is virtual consensus that hyperacidity and particularly hyperchlorohydria, i.e., hypersecretion of hydrochloric acid in the stomach, plus the presence of gastric pepsin are primarily responsible for the formation of gastric ulcer. Normally, the mucosal tissues of the stomach are protected by a film of mucin, the mucopolysacchride secreted by the gastric mucosa. It is theorized that the above-mentioned agents disturb the mucous membrane of the stomach and thereby give rise to the formation of ulcers. Accordingly, the heretofore proposed methods of treating the condition known as gastric ucler have focused completely upon counterbalancing the effect of excess hydrochloric acid together with other mineral acids and pepsin. Those modes of treatment which have been employed can be classified generally into the following groups: (1) application of antacid agents to neutralize the excess acid, such agents including conventional inorganic basic salts, colloidal neutralizing agents, anion exchange resins, amino acids, carboxymethylcellulose and the like; (2) application of anti-cholinergic agents; (3) the use of absorbents and adsorbents; and (4) introduction of agents to protect the mucous membrane of the stomach.

In accordance with the present invention, on the other hand, an entirely new method is provided for the treatment of gastric ulcer-prone patients in view of the recent evidence[1] that hyperchlorohydria may in fact not be the primary causative agent for gastric ulcer. It now appears that reflux of duodenal contents, especially bile, is an important etiologic factor in the formation of gastric ulcer. It has been found that the stomach of a patient with gastric ulcer contains bile more frequently and at higher concentrations than is found in the stomach of a normal subject. In an effort to explain this, studies have shown that in normal subjects, the pylorus functions as a sphincter which has the capacity to prevent retrograde movement of duodenal contents into the stomach. The human pylorus is associated with a zone of high pressure that relaxes with antral peristalsis, contracts with endogenous or exogenous hormonal stimulation, and regulates the regurgitation of duodenal contents into the stomach. It appears, therefore, that the failure or malfunction of the pylorus to function in its capacity as an effective sphincter in certain persons gives rise to the elevated gastric bile acid levels in the stomach and renders such a person prone to gastric ulcer.

[1] Fisher et al, *The New England Journal of Medicine*, 288, No. 6, pp. 273-276 (Feb. 8, 1973).

The present invention provides a method, entirely novel in its approach to treatment of the ulcer condition, which is directed toward counteracting the elevated levels of gastric bile acids caused by the aforementioned pyloric incompetence.

SUMMARY OF THE INVENTION

Accordingly, it is an object of the present invention to provide a method for the treatment of gastric ulcer-prone patients which effectively counteracts the physiological conditions contributing to the formation of gastric ulcer.

It is another object of the present invention to provide a method for the treatment of gastric ulcer-prone patients which is highly effective yet extremely simple to administer.

DETAILED DESCRIPTION OF THE INVENTION

In accomplishing the foregoing objects, there is provided in accordance with the present invention a method for treating a gastric ulcer-prone patient which comprises introducing into the stomach of the patient an effective amount of a non-toxic, non-absorbable active agent which will effectively bind both free and conjugated bile acids present in excess amounts in the stomach as a result of duodenogastric reguritation. In the preferred embodiment of the invention, the active agent is introduced into the stomach in combination with a buffering agent such as sodium bicarbonate, milk of magnesia, calcium carbonate, aluminum hydroxide gels, sulphated magnesium hydroxy aluminates, silicates and mixtures thereof. Typically, from 2,000 to 8,000 mgs. of the active agent are introduced into the stomach per day, in dosage forms each containing from 25 to 500 mgs. of active agent, most conveniently orally in the form of a tabletized preparation. The most preferred active agents are anion exchange resins having strong hydrophobic binding tendencies, for example, a styrene-divinylbenzene copolymer having quaternary ammonium functional groups attached thereto.

Although gastric ulcer formation has been ascribed to hyperacidity, emotional stress, genetic factors, etc., the exact causes or causes for the erosive process responsible for the breakdown of the gastric tissue is yet unclear. There is increasing evidence, however, that gastric resistance to crater formation is reduced by the presence of bile acids resulting from duodenal gastric reflux. It is believed that these bile acids are irritating to the gastric lining and can cause gastritis. It likewise appears that bile acids reduce the resistance of the stomach lining to attack by hydrogen ion.

In accordance with the present invention, the effect of the duodenal refluxate, i.e., primarily the bile acids contained therein, in the stomach is ameliorated by introducing into the stomach a non-toxic, non-absorbable active agent or agents which will effectively bind bile acids, both free and conjugated. There are a number of active agents which can be employed within the context of the present invention to reduce the effects of bile acid on the stomach. For example, in the presently most preferred embodiment of the invention, there are employed anion exchange resins which have a strong hydrophobic binding tendency and which do not release low molecular weight components when introduced into the stomach. Exemplary of these materials is a strongly basic anion exchange resin containing quaternary ammonium functional group attached to a styrene-divinylbenzene copolymer. Such strongly basic anion exchange resins are usually styrene-divinylbenzene copolymers in spherical bead form with quaternary ammonium groups incorporated in the structure.[2,3] The styrene-divinylbenzene copolymer is prepared by emulsion polymerization of styrene with divinylbenzene to produce spherical copolymer beads. These beads are chloromethylated with chloromethyl ether to incorporate chloromethyl groups into the polymer matrix. This chloromethylated polystyrene is treated with a tertiary amine to obtain the desired quaternary ammonium groups. The two most common commercial anion exchange resins are made with trimethylamine and dimethylethanolamine to yield the following ionic groups:

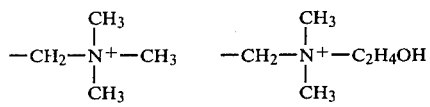

The U.S.P. grade used to remove bile acid from the intestine is called cholestyramine-U.S.P.

[2] Bauman, W. C., and Kellar, R. M. (The Dow Chemical Co.), U.S. Pat. No. 2,614,099 (1952).
[3] Bodamer, G. W. (Rohm and Hass Co.), U.S. Pat. No. 2,597,440 (1952)

Other suitable active agents which are useful in the context of the treatment method of the present invention include hydrophobic, nonionic polymeric adsorbents such as Amberlite XAD-2.[4] This is a synthetic insoluble crosslinked polystyrene polymer capable of adsorbing organic substances having hydrophobic and hydrophilic moieties in its molecular structure. This material is, therefore, particularly well suited to the removal of bile acids from the stomach.

[4] Rohm and Haas Co. Technical Bulletin, Amberlite XAD-2.

It will be appreciated that effective treatment of a gastric ulcer-prone patient can be accomplished by binding less than all of the bile acids present in the patient's stomach. Accordingly, because the level of excess bile acids will vary between different patients and because the degree of effectiveness of the various proposed active agents will also vary to a certain degree, it is difficult to define within precise limits the effective amount of active agent to be administered in accordance with the present treatment method. Generally speaking, however, successful treatment of an average gastric ulcer-prone patient may be achieved by administering from about 50 to 200 mgs. of the active agent to the stomach every 1 to 3 hours, particularly several hours after each meal when the ulcerogenic effect of refluxing bile acids would be increased. The protective action of the active agent will persist only as long as the agent remains in the stomach a period effectively limited to 1 to 3 hours. It is, therefore, desirable to maintain the protective coat provided by ingestion of the active agents by taking a number of small oral doses rather than infrequent large doses.

In another preferred aspect of the present invention, it is contemplated to introduce the active agent into a patient's stomach in combination with one or more buffering agents commonly used in antiacid preparation. Such buffering agents include such alkalizers as sodium bicarbonates, milk of magnesia, calcium carbonate, aluminum hydroxide gels, sulphated magnesium hydroxy aluminates, silicates and the like. Typically, the buffering agent is employed in an amount such that the weight ratio of the buffering agent to the active agent ranges between about 1:1 to about 4:1.

The preferred mode of application of the bile acid binding active agents according to the present invention is by oral intake. Therefore, the active agents may be suitably incorporated into the solid dosage forms either in powdered or tablet form. For example, the active agent in a dried finely divided state may be admixed with finely divided solid carriers, including any compatible diluent, incipient and/or binder tableting materials used in pharmaceuticals such as lactose, corn starch, talc, sugar, gelatin and other suitable gums and the like. Additionally, when tableting is contemplated, a small amount of a lubricant such as magnesium stearate is typically incorporated into the combination of ingredients. It is, of course, also possible to prepare semi-liquid formulations containing the active agents in accordance with the present invention. The additional buffering agents may likewise be incorporated in finely divided form into either the solid or semi-liquid dosage formulations described above.

By finely divided, it is contemplated that the active agent and optional buffering agents preferably be divided to from about 50 to about 100 mesh and even about 200 mesh or smaller, although it is possible that the ingredients be as large as about 20 mesh. Alternatively, the active ingredients may be admixed and encapsulated in capsules which are rapidly or at least readily frangible in the stomach, such as for example starch capsules.

The following specific examples are provided to more clearly describe the present invention, it being understood that the same are to be considered as merely illustrative and not in any manner limitative.

EXAMPLE I 200 grams of finely divided sucrose which has been wet granulated, dried and sieved in accordance with the known pharmaceutical art for preparation of sugar granulation is blended with 150 gms. of finely divided dried sulphated hydroxy magnesium aluminate, 100 gms. of finely divided, dried anion exchange resin (Cholestyramine Resin U.S.P.), 2.5 gms. of magnesium stearate (U.S.P.) and trace amounts of flavoring additives. The blend is tabletted in a conventional tabletting machine into 0.6 gram weight compressed tablets. To an adult patient experiencing discomfort from gastric reflux or having the symptoms of gastric ulcer are administered 12 such tablets on a daily basis whereupon relief from the gastric ulcer symptoms and healing of the ulcer is achieved.

Since the treatment is a prophylactic one with respect to the ulcer-prone individual, the patient is expected to be on the medication indefinitely. Conversely, the treatment effects an immediate alleviation of distress and promotes actual healing within 48 hours of an active or existing gastric ulcer in the patient already afflicted with same at the onset of treatment.

EXAMPLE II

To 100 parts of conventional oral liquid antacid preparation such as sold under the trade name of Maalox and Riopan, add one part of finely divided Cholestyramine Resin U.S.P. Two teaspoonsful of the resulting mixture are taken by those patients suffering from duodenal regurgitation, as required.

While the present invention has been described and pointed out with reference to but certain preferred embodiments thereof, it will be readily apparent to those of ordinary skill in the art that minor modifications may be made thereto without departing from the spirit of the present invention. Therefore, it is intended that the scope of the invention is to be limited only by the claims appended hereto.

What is claimed is:

1. A method for treating gastric ulcers in a patient afflicted with pyloric incompetence and concomitant duodenogastric regurgitation of bile acids, which method comprises periodically co-administering into the stomach of such patient (1) an effective, bile acid conjugating amount of a non-toxic, non-absorbable resinous active agent capable of effectively binding the free and conjugated bile acids present in the stomach as a result of said duodenogastric regurgitation, said resinous active agent being a hydrophobic, styrene-divinyl-benzene copolymer anion exchange resin bearing quaternary ammonium functional groups, together with (2) a bile acid buffering amount of a pharmaceutically acceptable alkalizer; and whereby there is thus counteracted the elevated level of such gastric bile acids in the stomach caused by said pyloric incompetence.

2. A method for treating gastric ulcers in a patient afflicted with pyloric incompetence and concomitant duodenogastric regurgitation of bile acids, which method comprises periodically co-administering into the stomach of such patient (1) an effective, bile acid conjugating amount of a non-toxic, non-absorbable resinous active agent capable of effectively binding the free and conjugated bile acids present in the stomach as a result of said duodenogastric regurgitation, said resinous active agent being a hydrophobic, cholestyramine anion exchange resin, together with (2) a bile acid buffering amount of a pharmaceutically acceptable aluminum hydroxide gel alkalizer; and whereby there is thus counteracted the elevated level of such gastric bile acids in the stomach caused by said pyloric incompetence.

3. The method of claim 1, wherein from 25 to 500 mgs. of said active agent are co-administered into the stomach per dose.

4. The method of claim 1, wherein said active agent is orally co-administered into the stomach.

5. The method of claim 4, wherein said active agent is in tablet form.

6. The method of claim 1, wherein from 2,000 to 8,000 mgs. of said active agent are co-administered into the stomach per day.

7. The method of claim 4, wherein said active agent is formulated in liquid form.

8. The method of claim 1, wherein said pharmaceutically acceptable alkalizer is a member selected from the group consisting of sodium bicarbonate, milk of magnesia, calcium carbonate, an aluminum hydroxide gel, a sulphated magnesium hydroxy aluminate, a silicate, and mixtures thereof.

9. The method of claim 1, wherein the effective amount of active agent is co-administered into the stomach during a period when the ulcerogenic effect of refluxing bile acids is enhanced.

10. The method of claim 1, wherein said patient is gastric ulcer-prone.

11. A pharmaceutical composition for the treatment of gastric ulcers in a patient afflicted with pyloric incompetence and concomitant duodenogastric regurgitation of bile acids, and suited for regulating the regurgitation of duodenal contents into the stomach, said composition essentially consisting of a unit dosage formulation of (1) an effective, bile acid conjugating amount of a non-toxic, non-absorbable resinous active agent capable of effectively binding the free and conjugated bile acids present in the stomach as a result of said duodenogastric regurgitation, said resinous active agent being a hydrophobic, styrene-divinyl-benzene copolymer anion exchange resin bearing quaternary ammonium functional groups, together with (2) a bile acid buffering amount of a pharmaceutically acceptable alkalizer.

12. A pharmaceutical composition for the treatment of gastric ulcers in a patient afflicted with pyloric incompetence and concomitant duodenogastric regurgitation of bile acids, and suited for regulating the regurgitation of duodenal contents into the stomach, said composition essentially consisting of a unit dosage formulation of (1) an effective, bile acid conjugating amount of a non-toxic, non-absorbable resinous active agent capable of effectively binding the free and conjugated bile acids present in the stomach as a result of said duodenogastric regurgitation, said resinous active agent being a hydrophobic, cholestyramine anion exchange resin, together with (2) a bile acid buffering amount of a pharmaceutically acceptable aluminum hydroxide gel alkalizer, and (3) a pharmaceutically effective inert carrier.

13. The composition of claim 11, wherein said pharmaceutically acceptable alkalizer is a member selected from the group consisting of sodium bicarbonate, milk of magnesia, calcium carbonate, an aluminum hydroxide gel, a sulphated magnesium hydroxy aluminate, a silicate, and mixtures thereof.

14. The composition of claim 13, wherein the effective amount of said active agent ranges from 25 to 500 mgs.

* * * * *